United States Patent [19]

Steinberg et al.

[11] Patent Number: 5,098,908
[45] Date of Patent: Mar. 24, 1992

[54] 17β-HYDROXYBENZOYL-4-AZA-5α-ANDROST-1-EN-3-ONES AS TESTOSTERONE REDUCTASE INHIBITORS

[75] Inventors: Nathan G. Steinberg, Clark; Gary H. Rasmusson, Watchung; Thomas N. Salzmann, North Plainfield, all of N.J.

[73] Assignee: Merck & Co., Inc., Rahway, N.J.

[21] Appl. No.: 540,966

[22] Filed: Jun. 20, 1990

[51] Int. Cl.$^5$ .................. A61K 31/58; C07J 73/00
[52] U.S. Cl. ..................... 514/284; 546/77
[58] Field of Search .................. 546/77, 78; 514/284

[56] References Cited

U.S. PATENT DOCUMENTS

| | | | |
|---|---|---|---|
| 2,227,876 | 7/1941 | Bolt | 546/77 |
| 3,239,417 | 3/1966 | Di Tullio et al. | 546/77 X |
| 3,264,301 | 8/1966 | Doorenbos et al. | 546/77 |
| 3,285,918 | 11/1966 | Doorenbos et al. | 544/246 |
| 4,220,775 | 2/1980 | Rasmusson et al. | 546/77 X |
| 4,317,817 | 3/1982 | Blohm et al. | 514/177 |
| 4,377,584 | 3/1983 | Rasmusson et al. | 546/77 X |
| 4,732,897 | 3/1988 | Cainelli et al. | 514/222 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,888,336 | 12/1989 | Holt et al. | 514/278 |
| 4,910,226 | 3/1990 | Holt et al. | 514/573 |

FOREIGN PATENT DOCUMENTS

| | | |
|---|---|---|
| 970692 | 7/1975 | Canada . |
| 0004949 | 10/1979 | European Pat. Off. . |
| 155096 | 9/1985 | European Pat. Off. . |
| 0277002 | 8/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 1465544 | 11/1965 | France . |

OTHER PUBLICATIONS

Endo, vol. 91, No. 2 (1972) by Neri, et al., pp. 427–437.
Steroids, 14, 269 (1969), by Nayfeh, et al.
Endo, vol. 92, p. 1216 (1973) by Voigt and Hsia.
J. Pharm. Sci., 62, 4, pp. 638–640 (1973) by Doorenbos and Solomons.
J. Pharm. Sci., 60, 8, pp. 1234–1235 (1971), by Doorenbos and Brown.
J. Pharm., 63, 4, pp. 620–622 (1974) by Doorenbos and Kim.
J. Med. Chem. (1986) 29 (11): pp. 2298–3115 by Rasmusson et al.
Prostate (1986) (1): pp. 65–75 by Brooks et al.
Steroids (1986) 47 (1): pp. 1–19 by Brooks et al.
Endocr. (1985) 117 (2): pp. 571–9, by Liang et al.
J. Med. Chem. (1984) 27 (12): pp. 1690–1701, by Rasmusson et al.

J. Org. Chem. (1981) vol. 46, No. 7, pp. 1442–1446 by Back.
Chem. Abstracts, vol. 95, 109055j, by T. Liang et al.
JNCI, vol. 74, No. 2, pp. 475–481 (Feb. 1985), by Kadahoma et al.
The Prostate, vol. 10, pp. 189–197 (1987) by G. L Andriole et al.
J. Endocr., vol. 57, pp. 111–121 (1973), by K. D. Bingham et al.
Toxicol. Appl. Pharmacol., vol. 103, pp. 222–227 (1990), by G. L. Kedderis et al.
Bioinorganic Chemistry, 17, pp. 372–376 (1986) by B. W. Metcalf et al.
Biochemistry, 1990, vol. 29, pp. 2815–2824, by M. A. Levy et al.
J. Med. Chem., 1990, vol. 33, pp. 943–950, D. A. Holt et al.

(List continued on next page.)

*Primary Examiner*—Diana G. Rivers
*Attorney, Agent, or Firm*—Salvatore C. Mitri; Charles M. Caruso

[57] ABSTRACT

Novel 17β-hydroxybenzoyl-4-aza-5α-androst-1-en-3-ones as tetosterone reductase inhibitors of the formula:

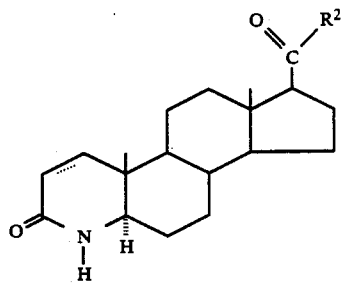

wherein
R is selected from hydrogen, methyl and ethy and
R$^2$ is phenyl substituted with one or more of: —OH, —OFC$_1$-C$_4$ alkyl, C$_1$-C$_4$ alkyl, —(CH$_2$)$_m$H, —(CH$_2$)$_n$ COOH, including protected —OH, where m is 1–4, n is 1–3, and providing C$_1$-C$_4$ alkyl is only present when one of the above oxygen containing radicals is present, wherein the dotted line represents a double bond which can be present, pharmaceutically acceptable salts and esters thereof, and a pharmaceutical formulation thereof. The above compounds are active as testosterone reductase inhibitors and thus are useful topically for treatment of acne, seborrhea, female hirsutism, and systemically in treatment of benign prostatic hypertrophy.

10 Claims, No Drawings

OTHER PUBLICATIONS

J. Steroid Biochem., vol. 34, Nos. 1-6, pp. 571-575 (1989), by M. A. Levy et al.

J. Med. Chem., vol. 33, pp. 937-942 (1990) by D. A. Holt et al.

TIPS, Dec. 1989, vol. 10, pp. 491-495, by D. W. Metcalf et al.

Steroids, vol. 35, No. 3 (Mar. 1980), p. 1-7.

Prostate, vol. 9, pp. 311-318 (1986) by N. Stone et al.

Steroids, vol. 47, No. 1, pp. 1-19 (1986) by J. R. Brooks et al.

Lancet, Nov. 1986, No. 8515, pp. 1095-1096 by Labrie et al.

J. Clin. Endocrin. and Metab., vol. 55, No. 1, pp. 188-193 (1987) by Rittmaster et al.

17β-HYDROXYBENZOYL-4-AZA-5α-ANDROST-1-EN-3-ONES AS TESTOSTERONE REDUCTASE INHIBITORS

BACKGROUND OF THE INVENTION

The present invention discloses novel 17β-hydroxybenzoyl-4-aza-5α-androst-1-en-3-ones and related compounds and the use of such compounds as testosterone-5α-reductase inhibitors.

DESCRIPTION OF THE PRIOR ART

The art discloses that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system.

Early attempts to provide a chemotherapeutic agent to counter the undesirable results of hyperandrogenicity resulted in the discovery of several steroidal anti-androgens having undesirable hormonal activities of their own. The estrogens, for example, not only counteract the effect of the androgens but have a feminizing effect as well. Non-steroidal anti-androgens have also been developed, for example, 4'-nitro-3'-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfe et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concommitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638–640 (1973); Doorenbos and Brown, J. Pharm. Sci., 60 8, pp. 1234–1235 (1971); and Doorenbos and Kim, J. Pharm. Sci. 63, 4, pp. 620–622 (1974).

In addition U.S. Pat. No. 4,377,584 and 4,220,775, 4,859,681, 4,760,071 and the articles J. Med. Chem. 27, p. 1690–1701 (1984) and J. Med. Chem. 29, 2998–2315 (1986) of Rasmusson et al., U.S. Pat. No. 4,845,104 to Carlin et al. and U.S. Pat. No. 4,732,897 to Cainelli, et al. describe 4-aza-17β-substituted-5α-androstan-3-ones which are said to be useful in the treatment of hyperandrogenic conditions. However, none of the cited references suggest that any of the novel 17βN-(monosubstituted)carbamoyl-4-aza-5α-androsten-1-en-3-ones of the present invention would have utility as highly potent testosterone-5α-reductase inhibitors.

SUMMARY OF THE INVENTION

The present invention is concerned with novel 17β-hydroxybenzoyl-carbamoyl-4-aza-5β-androsten-1-en-3-ones and related compounds, processes for their preparation, pharmaceutical formulations comprising the novel compounds as active ingredients and methods of inhibiting testosterone-5α-reductase and of treating hyperandrogenic conditions with the novel compounds or their pharmaceutical formulations.

In accordance with the present invention there is provided 17β-substituted benzoyl-4-aza-5α-androst-1-en-3-one compounds of the formula:

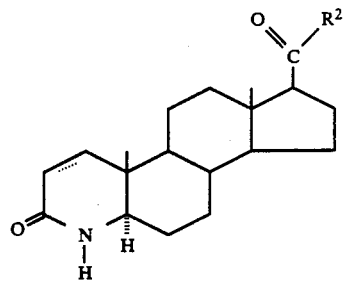

wherein
R is selected from hydrogen, methyl and ethyl and
$R^2$ is phenyl substituted with one or more of: —OH, —COOH, —O$C_1$–$C_4$ alkyl, $C_1$–$C_4$ alkyl, —($CH_2$)$_m$OH, —($CH_2$)$_n$ COOH, including protected OH, where m is 1–4, n is 1–3, providing $C_1$–$C_4$ alkyl is only present when one of the above oxygen-containing radicals is present, wherein the dotted line represents a double bond which can be present, and pharmaceutically acceptable salts and esters thereof.

Preferred embodiments of the novel 17β-acyl compounds of our invention are represented by the formula:

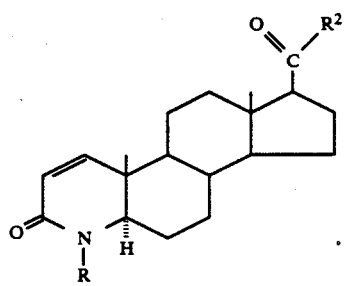

wherein
R is hydrogen, methyl or ethyl, and

R² is phenyl substituted with one or more —OH groups on the 2, 3, 4 or 5 positions of the phenyl ring.

In one class of this embodiment, R² is selected from the group consisting of hydroxyphenyl, dihydroxyphenyl, trihydroxyphenyl, hydroxyalkylphenyl, alkoxyphenyl, dialkoxyphenyl or carboxyalkyphenyl.

In another class of this embodiment, R is hydrogen and R² is phenyl substituted with hydroxy in the 2-, 3- or 4-position. In a preferred embodiment of this class, R² is protected hydroxy.

In a sub-class of this embodiment, R is hydrogen and R² is phenyl substituted with 4-hydroxy.

Representative compounds of the present invention include the following:

17β-(4-hydroxyphenylcarbonyl)-4-aza-5α-androst-1-en-3-one;
17β-(3-hydroxyphenylcarbonyl)-4-aza-5α-androst-1-en-3-one;
17β-(3,4-dihydroxyphenylcarbonyl)-4-aza-5α-androst-1-en-3-one;
17β-(3,5-dimethyl-4-hydroxyphenylcarbonyl)-4-aza-5α-androst-1-en-3-one;
17β-(4-hydroxymethylphenylcarbonyl)-4-aza-5α-androst-1-en-3-one;
17β-(2-hydroxyethylphenylcarbonyl)-4-aza-5α-androst-1-en-3-one;
17β-(4-methoxyphenylcarbonyl)-4-aza-5α-androst-1-en-3-one;
17β-(4-carboxymethylphenylcarbonyl)-4-aza-5α-androst-1-en-3-one;
17β-(4-hydroxyphenylcarbonyl)-4-aza-4-methyl-5α-androst-1-en-3-one;
17β-(3-hydroxyphenylcarbonyl)-4-aza-4-methyl-5α-androst-1-en-3-one;
17β-(3,4-dihydroxyphenylcarbonyl)-4-aza-4-methyl-5α-androst-1-en-3-one;
17β-(3,5-dimethyl-4-hydroxyphenylcarbonyl)-4-aza-4-methyl-5α-androst-1-en-3-one;
17β-(4-hydroxymethylphenylcarbonyl)-4-aza-4-methyl-5α-androst-1-en-3-one;
17β-(2-hydroxyethylphenylcarbonyl)-4-aza-4-methyl-5α-androst-1-en-3-one;
17β-(4-methoxyphenylcarbonyl)-4-aza-4-methyl-5α-androst-1-en-3-one;
17β-(4-carboxymethylphenylcarbonyl)-4-aza-4-methyl-5α-androst-1-en-3-one;
17β-(4-carboxyphenylcarbonyl)-4-aza-5α-androst-1-en-3-one;

and the corresponding compounds wherein the 4-hydrogen substituent is replaced in each of the above named compounds by a methyl or an ethyl radical.

Also included within the scope of this invention are pharmaceutically acceptable salts or esters, where a basic or acidic group is present on the adamantyl or norbornanyl moiety. When an acidic substituent is present, i.e. —COOH, there can be formed the ammonium, sodium, potassium, calcium salt, and the like, for use as the dosage form.

Where a basic group is present, i.e. amino, these acidic salts, i.e. hydrochloride, hydrobromide, acetate, pamoate, and the like, can be used as the dosage form.

Also, in the case of the —COOH group being present, pharmaceutically-acceptable esters can be employed, e.g. acetate, maleate, pivaloyloxymethyl, and the like, and those esters known in the art for modifying solubility or hydrolysis characteristics for use as sustained release or prodrug formulations.

The novel compounds of formula I of the present invention are prepared by a method starting with the known steroid ester of the formula:

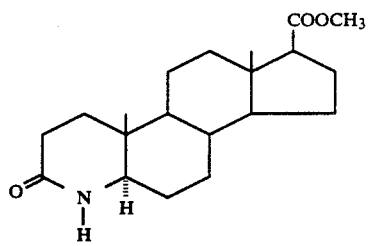

which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydrogenation step, it is preferable that the 4-aza nitrogen be unsubstituted. The dehydrogenation step can be carried out, e.g. according to the procedure of Dolling, et al. involving dichlorodicyanobenzoquinone, JACS (1988), Vol. 110, pp. 3318-3319. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an R²—Li or an R²MgX (X=Cl, Br) Grignard reagent such as p-methoxyphenyl-magnesium chloride in tetrahydrofuran to form the desired product, e.g. 17β-(p-methoxyphenylcarbonyl)-4-alkyl-4-aza-5α-androst-1-en-3-one (VIII) which is isolated by chromatography on silica gel. When this reaction is carried out using an R²MgX or, an R²—Li compound in place of p-methoxyphenyl-magnesium chloride, the corresponding 17β-(substituted benzoyl)-4-alkyl-4-aza-5α-androst-1-en-3one is prepared wherein phenyl is R².

The Grignard reagent, R²MgX, for all of the species included within the scope of this invention, are available and can be made readily by one skilled in the art.

For example, where R[2] is hydroxyphenyl, this can be derived by starting with an appropriate bromophenol, e.g. p-bromophenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

For R[2] being hydroxyethylphenyl, the same blocking procedure can be analogously conducted starting with the appropriate hydroxyalkyl bromophenol, e.g. p-hydroxymethylbromobenzene, or p-hydroxyethylbromobenzene.

Where R[2] is carboxyphenyl, this can be obtained by the chromic acid oxidation of the appropriate hydroxymethylbenzene, e.g. p-bromo-hydroxymethylbenzene, formed as described above.

Where R[2] is —O—$C_1$-$C_4$ alkyl, the appropriate bromo—O—$C_1$-$C_4$ alkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyl-dimethylsilyl, phenyldimethylsilyl, diphenylmethylsilyl, and the like.

By the term "$C_1$-$C_4$ alkyl" is used herein, is meant linear or branched alkyl, including methyl, ethyl, propyl, isopropyl, n-butyl, isobutyl, sec-butyl and t-butyl.

In accordance with the process of our invention, the corresponding 17β-benzoyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove, i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3one, (IX) which, in turn, is converted to the corresponding thio-pyridyl ester, 17β-(2-pyridylthiocarbonyl)-4-aza-5α-androstan-1one (X) followed by treatment of the ester with an R[2]MgX or R[2]Li compound wherein R[2] is as defined hereinabove to form a 17β-(substituted benzoyl)-4-aza-5α-androstan-3-one (XI) which is dehydrogenated as previously described to produce compound XIV, 17β-(acyl)-4-aza-5α-androst-1-en-3-one.

The above reactions are schematically represented in the following structural outline:

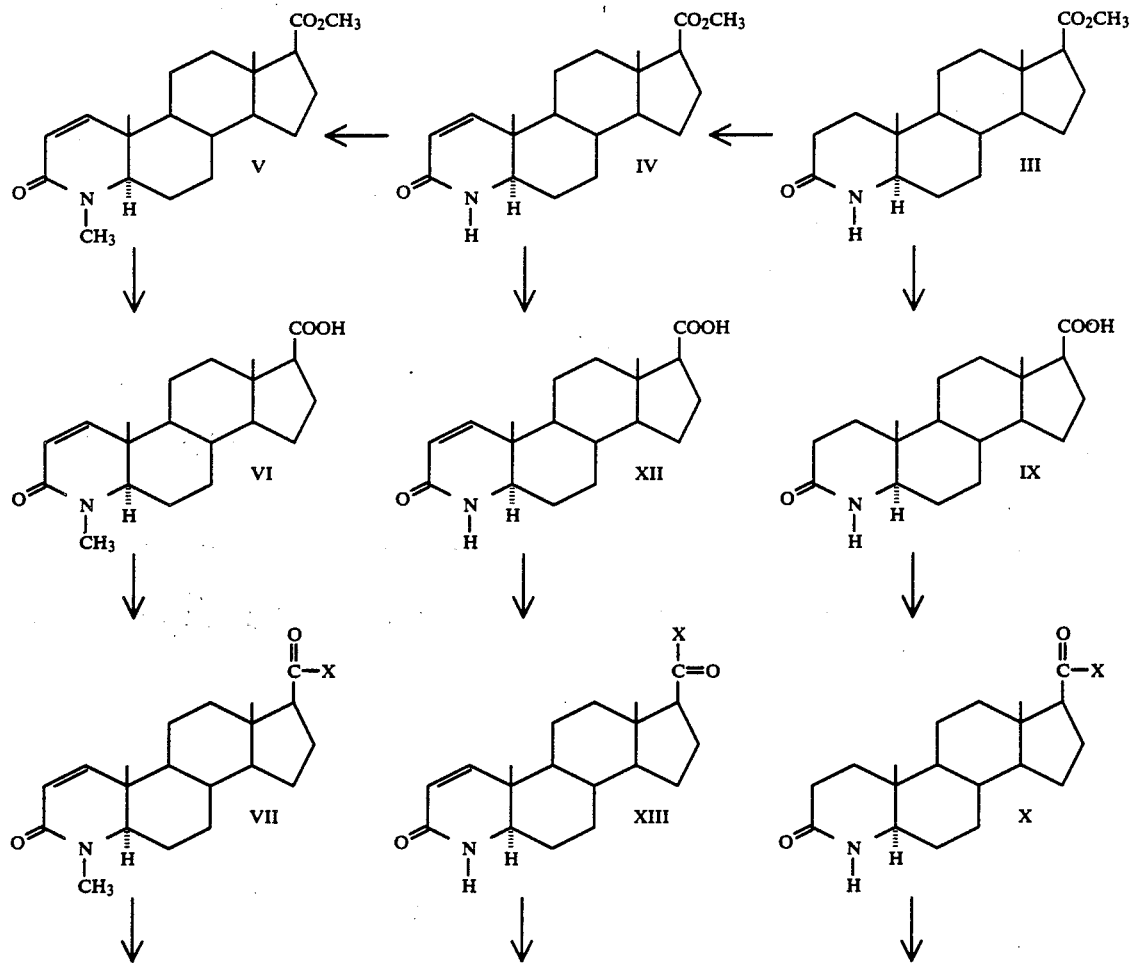

-continued

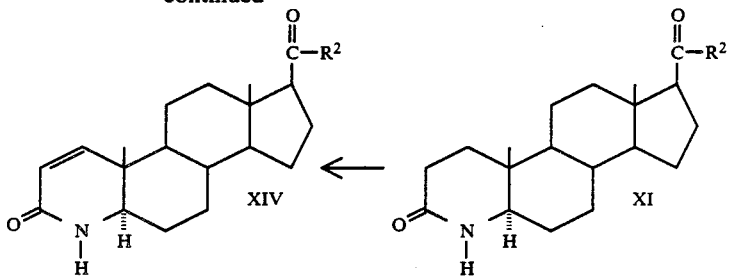

wherein X is a 2-pyridylthio substituent and R² is defined as hereinabove.

The compounds of the present invention, prepared in accordance with the method described above, are, as already described, potent antiandrogens by virtue of their ability to specifically inhibit testosterone-5α-reductase.

Also within the scope of the present invention are the ketone reduction products of I, the secondary alcohols of the formula:

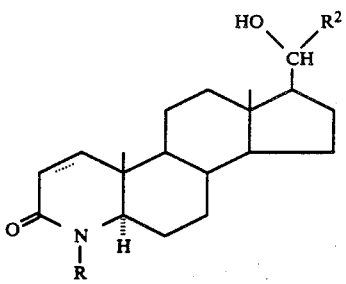

wherein

R is selected from hydrogen, methyl and ethyl, and
R² is phenyl substituted with one or more of —OH, —OC₁-C₄ alkyl, C₁-C₄ alkyl, —(CH₂)ₘOH, —(CH₂)ₙ COOH, including protected hydroxy, where m is 1-4, n is 1-3, providing C₁-C₄ alkyl is only present when one of the above oxygen-containing radicals is present, wherein the dotted line represents a double bond which can be present, and pharmaceutically acceptable salts and esters thereof.

These compounds can be made by conventional sodium borohydride reduction of the carbonyl attached to R² without reducing the amide carbonyl in Ring A or the 1,2-double bond, if present. If the R² phenyl contains a carbonyl function, it can be selectively blocked and then regenerated after the borohydride reduction by conventional methods.

The borohydride reduction can be carried out in, e.g. water or aqueous methanol, at a temperature of room temperature to 50° C. and the product then isolated and purified by conventional means. The compounds are also active as 5-alpha reductase inhibitors.

Accordingly, the present invention is particularly concerned with providing a method of treating the hyperandrogenic conditions of acne vulgaris, seborrhea, and female hirsutism by topical administration, and a method of treating all of the above conditions as well as benign prostatic hypertrophy, by oral or parenteral administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel 17β-N-monosubstituted or 17β acyl carbamoyl compounds of the present invention, already described above in general terms, may be further illustrated by the following examples.

GENERAL PROCEDURE FOR PREPARING PROTECTED SILYL DERIVATIVES 1.0 mole of phenol or its derivatives, or 1 mole of alcohol is treated with 1.5 liters of dry methylene chloride. To the clear solution is added dry 3.0 moles of imidazole/$N_2$. The clear solution is cooled to 0° C./$N_2$, and 2.0 moles of t-butyl dimethyl chlorosilane in 300.0 ml of dry methylene chloride is added dropwise at 0° C./$N_2$. Towards the end of the addition, precipitation occurs. The ice bath is removed, and the reaction is allowed to proceed overnight at R.T./$N_2$. Filter, wash the cake with cold $CH_2Cl_2$ solution, and the solvent is evaporated in vacuo to afford crude product. The crude product was readily purified by filtering through a silica gel column. (1 gr. of crude product per 100 g of silica gel, using $CH_2Cl_2$ as eluant) This method gives about 99% of pure silyl derivatives for phenols and alcohols.

EXAMPLE 1

Methyl 3-oxo-4-aza-5α-androst-1-ene-17β-carboxylate

A suspension of 83.7 g of methyl 3-oxo-4-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous $NaHCO_3$ solution and saturated NaCl solution, then dried and evaporated to leave 172.4 g. This material was chromatographed on 2.56 kg of silica gel eluting first with dichloromethane (5 liters) and then with 4:1 dichloromethane-eacetone. The desired product was eluted with 8 liters of the above-mixed solvent and evaporated in vacuo to yield 53.4 g. It was washed with diethyl ether and dried to leave 49.5 g of the above-titled product, m.p. 278°–280° C.

* See Rasmusson, Johnston and Arth. U.S. Pat. No. 4,377,584, Mar. 22, 1983.

EXAMPLE 2

S-(2-Pyridyl)-3-oxo-4-aza-5 α-androst-1-ene-17β-thiocarboxylate

A suspension of 25.0 g of the above product from Example 1 was saponified with 12.5 g of KOH in 150.0 ml of 5:1 $CH_3OH$—$H_2O$ under reflux conditions for 4 hours/$N_2$. The mixture was cooled to 25° C. and acidified to pH <2. Water (175 ml) was added gradually with stirring to leave a crystalline precipitate which was collected and washed with water.

After drying, the product amounted to 25 g., m.pt 313°–315° C. with decomposition.

The crude dry acid (23.0 g) was suspended in 210 ml of toluene, and to the suspension was added triphenylphosphine (56.0 g) and 2,2'-dipyridyl disulfide (48.3 g), and the mixture was stirred at 24° C. overnight/$N_2$. The reaction mixture was placed on a column of silica gel (1.3 kg) and was eluted with 1:1 (acetone/$CH_2Cl_2$). The desired thioester eluted slowly, and after rinsing with ether, yielded 36.8 g of the above-titled product, m.p. 232°–235° C.

EXAMPLE 3

Synthesis of 17-β-(4-Hydroxybenzoyl) -4-aza-5-α-androst-1-ene-3-one

A. Preparation of Grignard Reagent

To a suspension of 1.22 g of dry activated magnesium chips in 20.0 ml of dry THF was added 5.6 g of 1-bromo-4-tertiary-butyl dimethyl silyloxybenzene (prepared from p-bromophenol by the General Procedure detailed above) in 10.0 ml of THF under $N_2$. The reaction was run in an ultrasonic bath at a temperature range of 24°–30° C. To the well-agitated mixture was added dropwise 150 μl–200 μl of 1,2-dibromoethane/$N_2$. The reaction was allowed to proceed for 1–1½ hours at 28° C./$N_2$. The concentration of the Grignard reagent formed was 19.5 mmoles in 30.0 ml of dry THF.

The steroid from Example 2 (1.02 g, 2.49 mmoles) was suspended in 20.0 ml of dry THF, cooled to −80° C. and the above-prepared Grignard (11.5 ml; 3 equivalents) was added via syringe to the steroidal suspension in 5–10 minutes/$N_2$. The reaction was allowed to proceed for 1 hour at −80° C./$N_2$, and then at −10° C. for an additional hour/$N_2$. The reaction solution was diluted with 10.0 ml of methylene chloride and quenched with a saturated aqueous solution of $NH_4Cl$ to pH=4. Organic layers were separated, washed 3 times with $H_2O$, 3 times with saturated sodium chloride, dried over $MgSO_4$, filtered, and evaporated under a vacuum to a yellow color solid. Crystallization from ethyl acetate afforded 607 mg of product m.p. 248°–249° C.

Anal. Calcd. for $C_{31}H_{45}O_3NSi$: C,73.32; H,8.93; N,2.75. Found: C,73.27; H,8.99; N,2.75.

FAB: Found 508; Calc. 508.

B. Desilylation

Dissolved 1.3 g of product from above step A in 20.0 ml of dry THF. Cooled to −5° C. and added 437 μl of glacial acetic acid/$N_2$. To the cold solution at −5° C. was added via syringe 3.0 ml tetra-n-butyl-ammonium fluoride dropwise under $N_2$ atmosphere. Allowed the reaction to proceed under stirring for 1½–2 hours at 0° to −5° C./$N_2$. The reaction mixture was poured into a 2-layer mixture of ethyl acetate/sodium bicarbonate saturated solution at 0° C. The water layer was separated and further extracted with EtOAc 3 times and with $CH_2Cl_2$ (3 times).

The organic layers were combined, washed 3 times with $H_2O$, 1 time with saturated sodium chloride solution, and dried over $MgSO_4$, filtered and evaporated to dryness under vacuum. The crude product was crystallized from ethyl acetate to afford 977.9 mg, and further recrystallized from methanol to afford 842.3 mg of the above-titled product, m.pt. 296°–297° C.

Anal. Calcd. for $C_{25}H_{31}NO_3.1/3$ $H_2O$: C,75.15; H,7.98; N,3.51. Found: C,75.13; H,7.76; N,3.54.

(Mass Spec.) FAB: Found 394; Calcd. 394.

EXAMPLE 4

17-β-(3,5-dimethyl-4-hydroxybenzoyl)-4-aza-5α-androst-1-ene-3-one

A. Preparation of Grignard Reagent

To a suspension of 260.0 mg of dry activated magnesium chips in 6.0 ml of dry THF was added 628.0 mg of 1-bromo-3,5-dimethyl-4-tertiary-butyl-dimethyl-silyloxybenzene (prepared from 4-bromo-2,6-dimethylphenol by the General Procedure described above) in 4.0 ml of THF/N$_2$. The reaction was conducted in an ultrasonic bath at a temperature range of 24°–30° C. To the well-agitated mixture was added dropwise 40 μl of 1,2-dibromoethane/N$_2$. The reaction was allowed to proceed for 2 hours/N$_2$. The concentration of the Grignard reagent thus formed was 2 mmoles in 10.0 ml of dry THF.

The steroid from Example 2 (205.0 mg (0.5 mmoles) was suspended in 3.0 ml of dry THF, cooled to −80° C., and 7.5 ml of the above-prepared Grignard was introduced via syringe to the steroidal suspension over a period of 5–10 minutes/N$_2$. The reaction was allowed to proceed for 1 hour at −80° C./N$_2$ and then at −10° C. for additional hour/N$_2$.

The reaction was quenched with 1N HCl, and then diluted with chloroform. The organic layers were combined, washed 3 times with H$_2$O, 3 times with saturated sodium chloride and dried over MgSO$_4$, filtered and concentrated in vacuo. The crude residue was washed with ether to afford 121.7 mg of product.

The crude product was dissolved in 70:30 (CHCl$_3$-acetone), filtered through Teflon (Acrodisc CR) and purified by preparative HPLC (Waters Preppak) on silica gel and eluted with 70:30 (CHCl$_3$-acetone).

The major component was recrystallized from ethyl acetate to give 52.0 mg of product m.pt 245°–245.5° C.

Anal. Calcd. for C$_{33}$H$_{49}$O$_3$NSi: C,73.96; H,9.23; N,2.61 Found: C,74.06; H,9.33: N,2.64

(Mass Spec.) FAB: Found: 536; Calc.: 536

B. Deblocking the Silyl Derivative

Dissolved 54.0 mg of the above product from A in dry THF (1.3 ml). The clear solution was cooled to 0° C., and 29 μl of glacial HOAc was added via syringe/N$_2$. To the above solution was added dropwise 172 μl of tetra-n-butylammonium fluoride at 0° C. dropwise via syringe/N$_2$. Allowed the reaction to proceed at 0° C./N$_2$ for 1½ hours. The reaction mixture was poured into ice/saturated NaHCO$_3$ solution and EtOAc. Stirred for several minutes. Allow the layers to separate, and the H$_2$O layer was extracted 3 times with EtOAc and 3 times with CHCl$_3$.

Combined the organic layers and washed 3 times with H$_2$O, then 3 times with saturated NaCl, and then dried over MgSO$_4$, filtered and evaporated to dryness in vacuum to afford 52.2 mg.

The product was crystallized from EtOAc to give 22.5 mg of the above-titled product m.pt 305°–306° C.

Calc. for C$_{27}$H$_{35}$O$_3$N (Mass Spec.) FAB: Calc:422; Found: 422

EXAMPLE 5

Synthesis of
17-β-(4-Methoxybenzoyl)-4-aza-5-α-androst-1-ene-3-one

A. Preparation of Grignard Reagent

To a suspension of 258.0 mg of dry activated Mg chips in 8.0 ml of THF/N$_2$ was added 748.0 mg p-bromoanisole in 2.0 ml of dry THF. The reaction was run in an ultrasonic bath at a temperature range of 24°–30° C./N$_2$. To the well-agitated mixture was added dropwise 30.0 μl of 1,2-dibromoethane as a catalyst. The reaction was allowed to progress for 1–2 hours at 28° C. The formed Grignard reagent had a concentration of 4 mmoles in 10.0 μl of dry THF.

The steroid from Example 2 (205.0 mg (0.50 mml) was suspended in 2.0 ml of THF, cooled to −78° C. and the above-prepared Grignard reagent (3.75 ml; 3 equivalents) was added via syringe to the steroidal suspension over 5–10 minutes/N$_2$ and then at −10° C. for an additional hour/N$_2$. The resulting reaction mixture was a clear solution, which was cooled to 0°–5° C., diluted with chloroform and quenched with 1N HCl acid. The organic layers were separated, washed with H$_2$O 2 times, followed with saturated NaCl solution, dried over MgSO$_4$, filtered and evaporated in vacuo. The crude product was washed with ether, and crystallized from EtOAc to give 110 mg of product m.pt 305°–306° C.

Further purification was carried out by chromatographic isolation on a TLC. plate, (20 cm×20 cm×1000 μm), using as eluant, 70:30 (CHCl$_3$: acetone). Recrystallization from EtOAc yielded 78.56 mg of the above-titled product, m.pt 305°–306° C. (dec.).

(Mass Spec) FAB: Calcd.,408; Found 408.

EXAMPLE 6

Synthesis of
17-β-(3-hydroxybenzoyl)-4-aza-5α-androst-1-ene-3 one

A. Preparation of Grignard Reagent

To a suspension of 230.0 mg of dry activated Mg chips in 2.0 ml of dry THF was added 722.5 mg of 1-bromo-3-tertiary-butyl dimethyl-silyloxybenzene (prepared from 3-bromophenol by the General Procedure described above) in 8.0 ml of dry THF/N$_2$. The reaction was run in an ultrasonic bath at a temperature range of 24°–30° C./N$_2$. To the well-agitated mixture was added dropwise 20.0 μl of 1,2-dibromoethane/N$_2$. Allowed the reaction to progress for 2½ hours at 28°. C./N$_2$. The formed Grignard reagent had a concentration of 2.52 mmoles in 10.0 ml of dry THF.

The steroid from Example 2 (205.0 mg (0.5 mmoles) was suspended in 2.0 ml of THF, cooled to −78° C. and the above-prepared Grignard reagent (6.0 ml (3 equivalants)) was added via syringe to the steroidal suspension over 5–10 minutes/N$_2$, and then stirred for an additional hour at −10° C./N$_2$. The clear reaction mixture was quenched at 0° to −5° C. with 1N HCl acid for 10.0 minutes and diluted with CHCl$_3$. The combined organic layers were washed 3 times with H$_2$O, 3 times with saturated NaCl, and then dried over MgSO$_4$, filtered and concentrated in vacuo to afford crude product. The product was purified on silica gel column and was eluted with 70:30 (CHCl$_3$-acetone). The desired product amounted to 58.0 mg, as the silyl derivative, 17β-(3-tertiary-butyldimethylsilyloxybenzoyl)-4-methyl-4-aza-5α-androst-1-en-3-one.

B. Deblocking 57.6 mg of the above silyl derivative was dissolved in 3.0 ml of dry THF. The solution was cooled to 0° C., and 20 μl of glacial acetic acid was introduced via syringe. To the clear solution was added 130.0 μl of (n-butyl)$_4$NF via syringe, and allowed the reaction to proceed for 1 hour/N$_2$ at 0° C. The water layer was separated, extracted 3 times with EtOAc and then 3 times with chloroform. The organic layers were combined and washed 3 times with H$_2$O, 3 times with saturated NaCl solution, dried over MgSO$_4$, filtered and evaporated in vacuo to give 57.11 mg of crude product. The crude product was chromatographed by TLC (one plate, 20 cm×20 cm×250 μm silica gel), eluted with 70:30 (CHCl$_3$-acetone) to afford 44.5 mg of the above-titled product. Recrystallization from EtOAc gave 29.30 mg m.pt 279°–280° C.

Anal. Calcl. for $C_{25}H_{31}NO_3$: $8H_2O$: C,73.60; H,8.06; N,3.43. Found: C,73.26; H,8.22; N,3.28.

(Mass Spec.) FAB: Calcd: 394; Found 394.

EXAMPLE 7

Synthesis of 17-β-(4-hydroxymethylbenzoyl)-4-aza-5α-androst-1-en-3-one

A. Preparation of Grignard solution

To a suspension of 100.0 mg (4 mmoles) of dry activated Mg chips in 5.0 ml of dry $THF/N_2$, was added 753.0 mg (2.5 mmoles) of 1-bromo-4-tertiary-butyl dimethyl silyloxy methyl benzene (prepared from 4-bromobenzyl alcohol by the General Procedure described above). The reaction was conducted in an ultrasonic bath at a temperature range of 24°–30° $C./N_2$. To the well-agitated mixture was added 20 μl of 1,2-dibromoethane/$N_2$. Allowed the reaction to progress for 2 hours at 28° $C./N_2$. The concentration of formed Grignard was 2.5 mmoles in 5.0 ml of dry THF.

B. Grignard Reaction

The steroid from Example 2 (205.0 mg (0.5 mmoles) was suspended in 2.0 ml of THF, cooled to −78° C., and the above-prepared Grignard (3.0 ml, 3 equivalents) was introduced via syringe into the steroidal suspension over 5–10 minutes/$N_2$. Allowed the reaction to progress for 1 hour at −80° $C./N_2$, and then for an additional hour at −10° $C./N_2$. The clear reaction solution was quenched with saturated $NH_4Cl$ at 0° to −5° C., and then diluted with $CH_2Cl_2$. The organic layers were separated and washed 3 times with water, 3 times with saturated NaCl, dried over $MgSO_4$, filtered and evaporated in vacuo to dryness. Crude product was crystallized from EtOAc to give 137.8 mg of silyl product.

(Mass Spec.) FAB: Calcd.: 522; Found: 522.0.

C. Deblocking of Silyl Derivative

The product from Step B above (23.67 mg) was dissolved in 0.5 ml of THF and 0.5 ml of MeOH and cooled to 0° $C./N_2$. To the cold solution was added 10 μl of concentrated sulfuric acid (98%). The reaction was stirred for 45 minutes at 0° $C./N_2$. To the cold solution at 0° C. was slowly added a saturated solution of $NaHCO_3$ (3 times). The organic layer was collected and washed 3 times with water, 3 times with saturated solution of NaCl, dried over $MgSO_4$, filtered and evaporated to dryness in vacuo, to afford 10.18 mg. The crude product was crystallized from EtOAc to give 6.0 mg of the above-titled product, m.pt 318°–320° C.

Anal. Calcd. for $C_{26}H_{33}O_3N.1/3H_2O$: C,75.41: H,7.94; N,3.38. Found: C,75.61; H,7.84; N,3.12.

(Mass Spec.) FAB: Calc.: 408; Found: 408

EXAMPLE 8

Synthesis of 17-β-(4-Carboxybenzoyl)-4-aza-5α-androst-1-en-3-one

A. Oxidation 90.2 mg of the product from Example 7 was dissolved in 2.63 ml of glacial acetic acid and to the clear solution was added 69.0 mg of $CrO_3$ (previously dried over $P_2O_5$ at R.T. for 2 days in vacuo). After stirring overnight, the reaction mixture was diluted with water and allowed to age overnight in the refrigerator. The reaction mixture was filtered and the mother liquor and washes were extracted overnight using a water-EtOAc extractor, under reflux conditions. The organic layer was dried over $MgSO_4$, filtered and evaporated in vacuo. The residue was dissolved in hot MeOH, filtered and evaporated in vacuo to afford a product weighing 32.0 mg.

FAB: (Calc. for $C_{26}H_{31}O_4N$: 422.0; Found: 422.

B. Purification

The above free acid was purified by dissolving the above product in 1N sodium hydroxide solution. The clear solution was extracted 3 times with EtOAc. The aqueous basic solution was cooled and acidified with 1N HCl acid dropwise to pH=4 with stirring. The reaction mixture was allowed to age for 1 hour at 0° C. It was filtered and the residue was washed with cold water. Dried overnight to 100° C. in vacuum <0.2 mm pressure.

Yield of the above-titled free acid was 9.85 mg.

FAB: Calc. for $C_{25}H_{31}O_4N$: 422; Found 422.

NMR analysis indicated the product to be an acid.

C. Sodium Salt of Above Acid 4.9 mg of the above product acid B was dissolved in 2.0 ml of hot methanol. To the clear solution, was added 11.6 μl of 1N NaOH(aq). The solution was evaporated in vacuo nearly to dryness, addition 2.0 ml of water was added to reach pH 7.21. The aqueous solution was freeze dried to give 6.3 mg of the sodium salt of the above-titled product.

EXAMPLE 9

Synthesis of 17-β-(4-hydroxyethylbenzoyl)-4-aza-5α-androst-1-en-3-one

A. Grignard Reagent

To a suspension of 252 mg of dry activated Mg chips in 10.0 ml of dry THF was added 1.26 g (4 mmoles) of 1-bromo-4 tertiary-butyl dimethyl silyloxy ethyl benzene (prepared from 2-(p-bromophenyl) ethanol by the General Procedure described above). The reaction mixture was vigorously stirred using an ultrasonic vibrator/$N_2$. To the well-agitated mixture was added 40 μl of 1,2-dibromoethane to catalyze the above reaction. Allowed the reaction to progress for 3½–4 hours/$N_2$. The concentration of formed Grignard reagent was 4 mmoles in 10 ml of THF.

B. Grignard Reaction 205.0 mg (0.5 mmoles) of the aza-steroid of Example 2 was suspended in 2.0 ml of dry $THF/N_2$, cooled to −80° C., and the above-prepared Grignard (3.75 ml was added 3 equivalents) via syringe was introduced into the steroidal suspension over 5–10 minutes/$N_2$. The reaction was run at −80° C. for 1 hour/$N_2$ and then for an additional hour at −10° C. The reaction was quenched with a saturated solution of $NH_4Cl$ at 0°–5° C. and diluted with 10.0 ml of $CH_2Cl_2$. The organic layers were washed with water (3 times), saturated NaCl solution (3 times), dried with $MgSO_4$, filtered and evaporated in vacuo to dryness. The crude product was crystallized from EtOAc overnight to give 152.0 mg of product m.pt. 233°–234° C.

Anal. Calcd. for $C_{33}H_{49}O_3NSi$: ¼ $H_2O$: C,73.55; H,9.18, N,2.59. Found: C,73.45; H,8.94; N,3.21

FAB: Calc. 536; Found: 536

C. Desilylation 70.8 mg of product from Step B, was dissolved in 1.45 ml of methanol and 1.45 ml of THF. The solution was cooled to 0°–5° C. and 29 μl of conc. $H_2SO_4$ was added via syringe under $N_2$. The reaction was allowed to proceed for 45 minutes/$N_2$. The reaction was carefully quenched at 0° C. with a saturated solution of $NaHCO_3$, and extracted 3 times with $CH_2Cl_2$. The organic layers were separated, washed with water (3 times), then with saturated NaCl solution, dried over $MgSO_4$, filtered and evaporated in vacuo to give 43.0 mg of crude product. The crude product was placed on a column of silica gel and was eluted with 1:1 (acetone-$CH_2Cl_2$). The isolated product was crystallized from anhydrous methanol to afford 20.0 mg of the above-titled product m.pt 292°–293° C. with dec.

Anal. Calcd. for $C_{27}H_{35}O_3N.\frac{1}{4}$ $H_2$: C,75.31; H,3.25; N,3.25. Found: C,75.49; H,3.45; N,3.45.

FAB: Calcd 422; Found 422.

EXAMPLE 10

Synthesis of
17-β-(4-carboxymethylbenzoyl)-4-aza-5α-androst-1-en-3-one

A. Oxidation 13.0 mg of the product from Example 9 was dissolved in 1 ml of glacial acetic acid. To the clear solution was added 10.0 mg of $CrO_3$ (previously dried over $P_2O_5$ in vacuum at R.T.). Allowed the reaction to progress overnight at R. T., and then at 0° C. for 48 hours. The addition of 7.0 ml of water caused the product to crystallize overnight in a refrigerator. The crude product was isolated, washed with cold water and dried in a vacuum at 110° C. below 1 mm pressure.

The dried crude product was dissolved in 1N sodium hydroxide and the basic solution was extracted 3 times with methylene chloride (The organic layers were separated, and the aqueous basic solution was cooled and acidified with 1.5N hydrochloric acid. The precipitate was filtered, washed with water dried at 110° C. under vacuum at 0.1 mm pressure.

Yield of above-titled product = 7.0 mg.

FAB Calc. $C_{27}H_{33}O_4N$: 436; Found 436.

EXAMPLE 11

Synthesis of
17-β-(3,4-dihydroxybenzoyl)-4-aza-5α-androst-1-en-3-one

A. Grignard

To a suspension of 285 mg of dry activated magnesium chips in 10.0 ml of dry THF, was added 428 μl of 4-bromo-1,2-methylenedioxybenzene/$N_2$. (The starting material is commercially available from Aldrich Chemical) The reaction was conducted in an ultrasonic water bath at a temperature range of 24°–30° C. To the well-agitated mixture was added 40 μl of 1,2-dibromoethane as a catalyst/$N_2$, and the reaction was allowed to progress for 1½–2 hours at 28° C./$N_2$. The concentration of the formed Grignard reagent was 3.75 mmoles in 10 ml of dry THF.

The steroid from Example 2 (41 mg, 1 mmole) was suspended in 4.0 ml of dry THF/$N_2$ and cooled to −80° C. and 8.0 ml of the above-prepared Grignard (3 equivalents) was added via syringe to the steroidal suspension/$N_2$ over a period of 5-10 minutes. The reaction was allowed to proceed for 1 hour at −80° C., and then at −10° C. for an additional hour/$N_2$. The reaction mixture was diluted with $CH_2Cl_2$, and then quenched with 1N HCl at −5° C.

The organic layers were collected and washed with water 3 times, saturated NaCl solution 3 times, dried over $MgSO_4$, filtered and evaporated in vacuo to dryness. Purification of the crude product was carried out on 50.0 g of silica gel using as eluant 1:1($CH_2Cl_2$-acetone) to give 347.0 mg.

FAB showed 422; Calcd. 422.

62.4 mg of the above product was crystallized from EtOAc to afford 11.39 mg of product m.pt. 324°–325° C.

Anal. Calcd. for $C_{26}H_{31}O_4N.3/4$ $H_2O$: C, 71.78; H, 7.53; N, 3.22. Found: C, 71.90; H, 7.54; N, 3.25.

FAB for $C_{26}H_{31}O_4N$ showed 422; Calcd: 422.

B. Cleavage of Methylene Dioxylan Group 70.0 mg of the product from Step A was dissolved in dry 25.0 ml of 1,2-dichloroethane at R.T./$N_2$. The solution was allowed to cool to −10° C., and 1.03 ml of $BBr_3$ (1.0M solution in dichloromethane) was added dropwise under $N_2$ atmosphere. The reaction was allowed to proceed at R.T. for 3½–4 hours/$N_2$. After 4 hours/$N_2$, the reaction was cooled to (−10° C.) and quenched with 10.0 ml of methanol for 10 minutes at 0° C., and then gradually the temperature was allowed to rise to R.T./$N_2$. The reaction mixture was evaporated in vacuo to dryness. The residue was extracted 3 times with EtOAc. The organic layers were washed with water 3 times, 2 times with saturated $NaHCO_3$ solution, 3 times with water and finally with a saturated solution of NaCl. The organic layers were dried over magnesium sulfate, filtered and concentrated in vacuo. The crude material was chromatographed on 2 silica gel plates, (20 cm×20 cm×20 cm×250 μm) eluted with 1:1 (acetonemethylene chloride). Recrystallization from EtOAc afforded 5.0 mg of the above-titled product m.p. 222°–222.5° C.

Anal. Calcd. for $C_{25}H_{31}O_4N. \frac{1}{2}$ $H_2O$: C, 71.78; H, 7.66; N, 3.35. Found: C, 71.71; H, 7.71; N, 3.33.

FAB: Calcd. for $C_{25}H_{31}O_4N$: 410; Found 410.

EXAMPLE 13

Synthesis of 17-β-(2 methoxy-benzoyl)-4-aza-5α-androst-1-ene-3-one

A. Grignard

To a suspension of 258.0 mg of dry activated magnesium chips in 8.0 ml of dry THF was added 771.0 mg of o-bromoanisole in 2.0 ml of dry THF/$N_2$. The reaction was conducted in an ultrasonic water bath at a temperature range of 24°–30° C. To the well-agitated mixture was added 30 μl of 1,2-dibromoethane/$N_2$, and the reaction was allowed to progress for 2 hours at 28° C./$N_2$. The concentration of the formed Grignard reagent was 4 mmoles in 10.0 ml of dry THF.

The steroid from Example 2 (205 mg, 0.5 mmoles) was suspended in 2.0 ml of dry THF/$N_2$, cooled to −79° C., and 4.0 ml of the above-prepared Grignard (3 equivalents) was added via syringe to the steroidal suspension/$N_2$ over a period of 5-10 minutes. The reaction mixture was allowed to proceed for 1 hour at −80° C., and then at 0°–2° C. for an additional hour/$N_2$. The reaction mixture was diluted with $CH_2Cl_2$ and then quenched with 1N HCl solution at 0° C.

The organic layers were combined, washed 3 times with water, 3 times with saturated NaCl solution; and dried over MgSO$_4$. Filtered and evaporated in vacuum to dryness. The crude material was crystallized from EtOAc to give 124.5 mg of product m.pt 228°–230° C. Purification on silica gel column using 70:30 (CHCl$_3$-acetone) gave a single spot material in a yield of 83.0 mg m.pt. 241–241.5.

Anal. Calcd. for C$_{26}$H$_{33}$O$_3$N: C,76.91; H,8.19; N,3.95. Found: C,76.36; H,8.26; N,3.35.

FAB calcd. for C$_{26}$H$_{33}$O$_3$: 406; Found: 406.

B. Cleavage of Methoxy Group 12.7 mg (0.03 mmoles) of the product from Step A was dissolved in 5.0 ml of dry methylene chloride/N$_2$. To clear solution at −79° C./N, was added 50 μl of 1 mmole/ml of BBr$_3$ in CH$_2$Cl$_2$ via syringe dropwise. Allowed the reaction to proceed at R.T. overnight/N$_2$ with rapid stirring. Next day, a clear yellow solution was obtained. The reaction mixture was cooled to 0°–2° C. and quenched with water, to hydrolyze excess of BBr$_3$. The organic phase was washed 3 times with dilute sodium hydroxide, 3 times with water, 3 times with dilute HCl, 3 times with water, 3 times with saturated NaCl solution, and dried the organic layer over MgSO$_4$. Filtered, concentrated in a vacuum to dryness. The crude product crystallized from EtOAc to afford 7.0 mg of a pure single spot material being 17-β-(2-hydroxymethyl-benzoyl)-4-aza-5-α-androst-1-en-3-one.

FAB for C$_{25}$H$_{31}$NO$_2$; Calcd: 394; Found: 394.

EXAMPLE 14

17β(α-hydroxy benzyl)-4-aza-5α-androst-1-ene-3-one 570 mg of 17β-benzoyl-4-aza-5α-androst-1-ene-3-one (prepared from the thiopyridyl ester of Example 2 and commercially available phenyl magnesium bromide, 3 equivalents, analogously via the procedure in Example 3, second paragraph, to produce the 17-benzoyl derivative, mp. 295°–296° C. crystallized from EtOAc) was suspended in 80 ml of anhydrous isopropanol. To the suspension was added 500.0 mg of NaBH$_4$ in 5 portions. When all the hydride was added, 20.0 ml of dry THF was carefully added, so that the reaction mixture became a clear solution. Allowed the reaction mixture to proceed at R.T./N$_2$ overnight. The reaction was quenched carefully with 1N HCl, and allowed to stir under N$_2$ for an additional hour at R.T. It was then diluted with water, and extracted 3 times with CHCl$_3$. The organic layers were combined, washed 3 times with H$_2$O; 3 times with saturated NaCl solution, and dried over MgSO$_4$. Filtered and evaporated to a white solid weighing 575.0 mg.

The crude material was crystallized from EtOAc to afford 390.0 mg of material m.pt. 299°–301° C. Further purification on a silica gel column, using as eluant, 70:30 (CHCl$_3$-acetone) gave a single spot material, 360.0 mg, of the above-titled compound, m.pt 305°–306° C.

Anal. Calcd. for C$_{25}$H$_{33}$NO$_2$: C,79.17; H,8.78; N,3.70. Found: C,79.24; H,8.85; N,3.48.

FAB Calcd. for C$_{25}$H$_{33}$NO$_2$: 380; Found: 380.

EXAMPLE 15

17β-hydroxymethyl-4aza-5α-androst-1-ene-3-one 500.0 mg of S-2-pyridyl-3-oxo-4aza-5α-androst-1-ene-3 one (Example 2) was dissolved in 40.0 ml of dry THF at R.T./N$_2$. The solution was cooled to −78° C./N$_2$ and 5.5 ml of 1M dibutyl aluminium hydride in THF was slowly added via syringe to the solution, with rapid stirring. Allowed the reaction to proceed at −76° to −78° C. for half an hour under N$_2$. The temperature was gradually brought to R.T. and the reaction mixture kept for 2½ hours/N$_2$. The reaction was then quenched at 0° to 5° C. with 2N HCl acid, and then diluted with CHCl$_3$. The organic layers were separated, washed with H$_2$O 3 times, then with saturated NaCl solution, and finally dried over MgSO$_2$. Filtered, and the organic phase was evaporated under vacuum to give 216.0 mg of crude product.

The crude product was chromatographed on 20.0 g of E.M. silica gel column, using 70:30 (CHCl$_3$-acetone) as eluant.

Yield of single spot material was 126.3 mg of the above-titled compound, m.pt. 271°–271.5° C.

Calcd. for C$_{19}$H$_{29}$O$_2$N: FAB 304; Found 304.

NMR in CDCl$_3$ confirmed the above structure.

EXAMPLE 16

17β-Formyl-4 aza-5a-androst-1-ene-3-one

Into a 100.0 ml dry flask was placed 1.3 ml of oxalyl chloride (2M in CH$_2$Cl$_2$) with 50.0 ml of dry CH$_2$Cl$_2$/N$_2$. The above solution was cooled to −78° C. and 338 μl of DMSO was added dropwise via syringe/N$_2$. The mixture was stirred at −78° C./N$_2$ for 30 minutes, and a solution of above-prepared alcohol from Example 15, i.e. 17β hydroxymethyl-4-aza-5α-androst-1-ene-3-one (256.9 mg in 15.0 ml of dry CH$_2$Cl$_2$/N$_2$ was added via syringe. The reaction was allowed to progress for one hour at −78° C./N$_2$. After an hour at −78° C., was added 1 ml of dry triethylamine at a rapid rate. Reaction was raised slowly to R.T./N$_2$ with stirring, the resulting yellow solution was then poured into 50.0 ml of cold water. The organic layers were washed with a saturated solution of NaHCO$_3$, and then with a saturated solution of NaCl. Dried over MgSO$_4$, evaporated the solvent under vacuum to give 172.4 mg of crude product. The crude product was chromatographed on 60.0 g silica gel column using 70.30 (CHCl$_3$-acetone), to give a single spot material. Crystallization from EtOAc afforded the above-titled compound, 37.7 mg, m.pt. 258°–259° C.

EXAMPLE 17

Synthesis of diastereoisomeric 17β(α-hydroxy) benzyl)-4 aza-5a androst-1-ene-3-ones 26.3 of above-prepared formyl derivative (from Example 16) was dissolved in 7.0 ml of dry THF/N$_2$. The solution was cooled to −78° C./N$_2$, and 131 μl of phenyl magnesium bromide (Aldrich reagent) (3 equivalents) in dry THF was added dropwise via syringe/N$_2$. Allowed the reaction to proceed for 1 hour/N$_2$ at −78° C. and then at R.T. for addition hour/N$_2$.

The reaction was quenched at 0°–5° C. with 2.5N HCl, and then diluted with CHCl$_3$. Organic layers were separated, washed 3 times with water; 3 times with saturated NaCl solution, dried over MgSO$_4$. Filtered and evaporated in vacuum to dryness to afford 28.6 mg of crude product. The crude product was filtered through a 1 μm Teflon filter and purified by HPLC on a Whitman Portisil 10 column using 70:30 (CHCl$_3$-acetone). NMR analysis, as well as, peak heights from HPLC analysis indicated this product to be a 1:1 mixture of diastereoisomers. The FAB mass spectrum clearly indicated correct M$^+$+1 for both isomers, namely 380 units. The polar isomer whose purity was 99.5%, m.pt. 289°-289.5° C., was crystallized from EtOAc and showed a single spot material on TLC.

Anal. Calcd. for $C_{25}H_{33}NO_2 \cdot \frac{1}{4} H_2O$; C,78.39; H,8.81; N,3.65. Found: C,78.11; H,8.65; N,3.58.

The less polar isomer whose purity was 98%, m.pt. 300°-301° C. showed a single spot material on TLC. The polar isomer showed by NMR(CDCl$_3$): CH$_3$ at C-18 was deshielded (0.89 $\delta$) as compared to the less polar CH$_3$ at C-18 at (0.69 $\delta$). The other interesting observation, the benzilic proton for the polar isomer was also deshielded (4.5 $\delta$) versus (4.95 $\delta$). The olefinic proton at C-1 showed deshielding effects for the polar isomer at (6.81 $\delta$) to (6.62 $\delta$). From the above data, the two isomers showed distinctly different physical properties.

What is claimed is:

1. A compound of the formula:

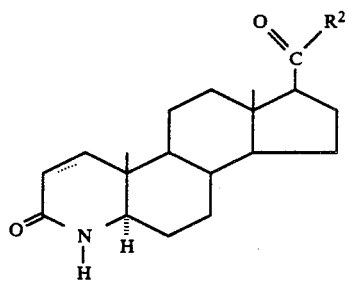

wherein

R is selected from hydrogen, methyl and ethyl, and R$^2$ is phenyl substituted with one or more of —OH, —COOH, —OC$_1$-C$_4$ alkyl, C$_1$-C$_4$ alkyl, —(CH$_2$)$_m$OH, —(CH$_2$)$_n$ COOH, including protected hydroxy, where m is 1-4, n is 1-3, providing C$_1$-C$_4$ alkyl is only present when one of the above oxygen-containing radicals is present, wherein the dotted line represents a double bond which can be present, and pharmaceutically acceptable salts and esters thereof.

2. The compound of claim 1 having the formula:

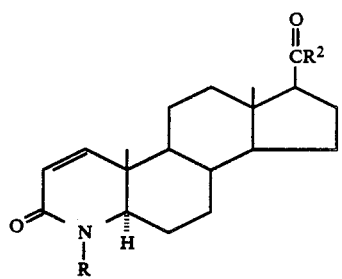

wherein

R$_2$ is hydrogen, methyl or ethyl and
R$^2$ is hydroxyphenyl, dihydroxyphenyl, trihydroxyphenyl, hydroxyalkylphenyl, alkoxyphenyl, dialkoxyphenyl or carboxyalkylphenyl.

3. The compound of claim 1 wherein R$^2$ is phenyl substituted with hydroxy in the 2-, 3-, or 4-position and R is hydrogen.

4. The compound of claim 3 wherein R$^2$ is protected hydroxy.

5. The compound of claim 2 wherein R$^2$ is phenyl substituted with hydroxy in the 2-, 3- or 4-position and R is hydrogen.

6. The compound of claim 5 wherein R$^2$ is phenyl substituted with 4-hydroxy.

7. The compound of claim 1 wherein the compound is:

17$\beta$-(4-hydroxyphenylcarbonyl)-4-aza-5$\alpha$-androst-1-en-3-one;
17$\beta$-(3-hydroxyphenylcarbonyl)-4-aza-5$\alpha$-androst-1-en-3-one;
17$\beta$-(3,4-dihydroxyphenylcarbonyl)-4-aza-androst-1-en-3-one;
17$\beta$-(3,4-dihydroxyphenylcarbonyl)-4-aza-androst-1-en-3-one;
17$\beta$-(3,5-dimethyl-4-hydroxyphenylcarbonyl)-4-aza-5$\alpha$-androst-1-en-3-one;
17$\beta$-(4-hydroxymethylphenylcarbonyl)-4-aza-5$\alpha$-androst-1-en-3-one;
17$\beta$-(4-methoxyphenylcarbonyl)-4-aza-5$\alpha$-androst-1-en-3-one;
17$\beta$-(2-hydroxyethlphenylcarbonyl)-4-aza-5$\alpha$-androst-1-en-3-one;
17$\beta$-(4-methoxyphenylcarbonyl)-4-aza-5$\alpha$-androst-1-en-3-one
17$\beta$-(4-carboxymethylphenylcarbonyl)-4-aza-5$\alpha$-androst-1-en-3-one;
17$\beta$-(4-hydroxyphenylcarbonyl)-4-aza-4-methyl-5$\alpha$-androst-1-en-3-one;
17$\beta$-(3-hydroxyphenylcarbonyl)-4-aza-4-methyl-5$\alpha$-androst-1-en-3-one;
17$\beta$-(3-4-dihydroxyphenylcarbonyl)-4-aza-4-methyl-5$\alpha$-androst-1-en-3-one;
17$\beta$-(3-5-dimethyl-4-hydroxyphenylcarbonyl)-4-aza-4-methyl-5$\alpha$-androst-1-en-3-one;
17$\beta$-(4-hydroxymethylphenylcarbonyl)-4-aza-4-methyl-5$\alpha$-androst-1-en-3-one;
17$\beta$-(2-hydroxyethylphenylcarbonyl)-4-aza-4-methyl-5$\alpha$-androst-1-en-3-one;
17$\beta$-(4-methoxphenylcarbonyl)-4-aza-4-methyl-5$\alpha$-androst-1-en-3-one;
17$\beta$-(4-carboxymethylphenylcarbonyl)-4-aza-4-methyl-5$\alpha$-androst-1-en-3-one; or
17$\beta$-(4-carboxyphenylcarbonyl)-4-aza-5$\alpha$-androst-1-en-3-one.

8. A method of treating the hyperandrogenic condition of acne vulgaris, seborrhea, female hirsutism, and benign prostatic hypertrophy comprising parenteral administration to a patient in need of such treatment of a therapeutically effective amount of a compound of formula:

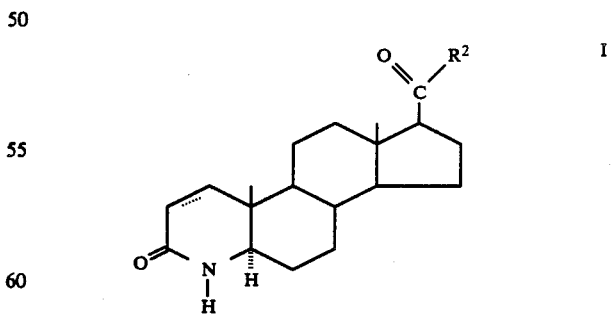

wherein

R is selected from hydrogen, methyl and ethyl, and R$^2$ is phenyl substituted with one or more of: —OH, —COOH, —OC$_1$-C$_4$ alkyl, C$_1$-C$_4$ alkyl, —(CH$_2$)$_m$OH, —(CH$_2$)$_n$ COOH, including protected —OH, where m is 1-4, n is 1-3, providing C$_1$-C$_4$ alkyl is only present when one of the above oxygen-containing radicals is present, wherein the dotted line represents a double bond which can be present, and pharmaceutically acceptable salts and esters thereof.

9. A pharmaceutical composition comprising of a pharmaceutically acceptable carrier and a therapeutically effective amount of a compound according to claim 1.

10. A compound of the formula:

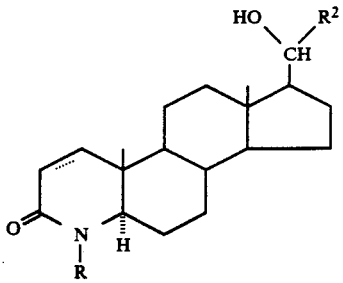

wherein
R is selected from hydrogen, methyl and ethyl, and
R² is phenyl substituted with one or more of —OH, —OC₁-C₄ alkyl, C₁-C₄ alkyl, —(CH₂)ₘOH, —(CH₂)ₙ COOH, including protected —OH, where m is 1-4, n is 1-3, providing C₁-C₄ alkyl is only present when one of the above oxygen-containing radicals is present, wherein the dotted line represents a double bond which can be present, and pharmaceutically acceptable salts and esters thereof.

* * * * *